United States Patent [19]

Marchand et al.

[11] Patent Number: 5,602,031
[45] Date of Patent: Feb. 11, 1997

[54] DNA ENCODING MOLECULES CONTAINING AT LEAST ONE PEPTIDE SEQUENCE CARRYING ONE OR SEVERAL EPITOPES CHARACTERISTIC OF A LIVER STAGE ANTIGEN PRODUCED BY P. FALCIPARUM IN HEPATOCYTES AND COMPOSITIONS CONTAINING THEM

[75] Inventors: Claudine Marchand, Paris; Pierre Druilhe, Saint Mande; Odile Puijalon-Mercereau, Issy les Moulineaux; Gordon Langsley, Paris, all of France

[73] Assignee: Institut Pasteur, Paris, France

[21] Appl. No.: 462,062

[22] Filed: Jun. 5, 1995

Related U.S. Application Data

[62] Division of Ser. No. 275,139, filed as PCT/FR88/00074, Feb. 9, 1988 published as WO88/05785, Aug. 11, 1988.

[30] Foreign Application Priority Data

Feb. 9, 1987 [FR] France .................................. 87 01543

[51] Int. Cl.⁶ .................. C07H 21/04; C12N 15/30; C07K 14/445
[52] U.S. Cl. ............. 435/252.3; 435/69.3; 435/320.1; 536/23.4; 536/23.5; 424/191.1; 424/268.1; 424/272.1; 530/350; 530/395
[58] Field of Search ................ 536/23.5, 23.4; 530/350, 395; 424/268.1, 272.1, 191.1; 435/69.3, 252.3, 320.1

[56] References Cited

FOREIGN PATENT DOCUMENTS

| 88/05785 | 8/1988 | WIPO | C07K 7/08 |
| 90/06130 | 6/1990 | WIPO | A61K 39/015 |
| 92/1388 | 8/1992 | WIPO | C07K 13/00 |

OTHER PUBLICATIONS

Druilhe, P. et al., Am. J. Trop. Med. Hyg. 33(3):336–341, "Species-and state-specific antigens in exoerytrhocytic stages of *Plasmodium falciparum*".

Fidock, D. A. et al., J. Immunology 153:190–204, "*Plasmodium falciparum* liver stage antigen–1 is well conserved and contains potent B and T cell determinants".

Guerin–Marchand, C. et al., Nature 329:164–167, "A liver-stage-specific antigen of Plasmodium falciparum characterized by gene cloning".

Shortt, H. E. et al., Transactions of the Royal Society of Tropical Medicine and Hygiene 41(6):785–795, "The pre-erythrocytic development of Plasmodium cynomolgi and Plasmodium vivax".

Zhu, J. et al. Mol. Biochem. Parasitol. 48:223–226, "Structure of *Plasmodium falciparum* liver state antigen–1".

Kochan et al., "A Tandemly Repeated Sequence Determines the Binding Domain for an Erythrocyte Receptor Binding Protein of *P. falciparum*", Cell, vol. 44, pp. 689–691 (Mar. 1986).

Ravetch et al, "Isolation of the Gene for a Glycophorin–Binding Protein Implicated in Erythrocyte Invasion by a Malaria Parasite", Science, vol. 227, pp. 1593–1597 (Mar. 1985).

Druilhe et al., Biological Abstracts, vol. 78, No. 8, p. 6756, abstract 59971 (1984).

Hussain et al., Biological Abstracts, vol. 67, No. 8, p. 4780, abstract 47958 (1976).

Walter & Eliza Hall Institute of Medical Research, PCT publication WO 84/02917 (1984).

Hussain et al., Biological Abstracts, vol. 67, no. 8, p. 4780, abstract 47957 (1976).

Miller et al., Science, vol. 234, pp. 1349–1356 (1986).

Marchand et al., Nature, vol. 329, No. 6135, pp. 164–167 (Sep. 1987).

*Primary Examiner*—Thomas M. Cunningham
*Attorney, Agent, or Firm*—Burns, Doane, Swecker & Mathis, L.L.P.

[57] ABSTRACT

The invention relates to a molecule comprising one or more peptide sequences of formula:
Leu-Ala-Lys-Glu-Lys-Leu-Gln-X-Gln-Gln-Ser-Asp-Leu-Glu-Gln-Glu-Arg
in which X is Glu or Gly.

It also relates to the utilisation of these molecules in assays and in vitro diagnostic kits for malaria on a biological sample derived from the individual in whom the disease is to be detected.

7 Claims, 2 Drawing Sheets

DNA SEQUENCE CONTAINED IN THE CLONE 307

GAATTCC-GACTTGCTAAAGAAAAAGTTACAAGAGAGCAGCAAAGCGATTTAGAACAAGAGAGA
Eco RI Adaptor

CTTGCTAAAGAAAAAGTTGCAAGAACAACAAAGCGATCTAGAACAAGAGAGA
                                    Sau3A

CTAGCTAAAGAAAAAGTTACAGGGGCAACAAAGCGATCTAGAACAAGAGAGA
Alu1                                Sau3A

CTTGCTAAAGAAAAAGTTGCAAGAACAACAAAGCGATTTAGA-GAATTCC
                                           Eco RI Adaptor

*Figure 1*

SEQUENCE OF AMINO ACIDS CONTAINED IN THE CLONE 307

Eco RI Adaptor
GAA TTC CGA
glu phe arg  leu ala lys glu lys leu gln glu gln gln ser asp leu glu gln glu arg leu ala lys glu lys leu gln glu gln gln ser asp leu glu gln glu arg leu ala lys glu lys leu gln gly gln gln ser asp leu glu gln glu arg leu ala lys glu lys leu gln glu gln gln ser asp leu glu
                                                                     GAG AAT TCC
                                                                     Eco RI Adaptor

*Figure 2*

DNA ENCODING MOLECULES CONTAINING AT LEAST ONE PEPTIDE SEQUENCE CARRYING ONE OR SEVERAL EPITOPES CHARACTERISTIC OF A LIVER STAGE ANTIGEN PRODUCED BY *P. FALCIPARUM* IN HEPATOCYTES AND COMPOSITIONS CONTAINING THEM

This application is a divisional of application Ser. No. 07/275,139, filed as PCT/FR88/00074, Feb. 9, 1988, published as WO88/05785, Aug. 11, 1988.

The parasites responsible for malaria in man, especially *Plasmodium falciparum* and *Plasmodium vivax* to mention only the principal ones among them, exhibit various morphologies in the human host and express different antigens depending on their localization in the organism of the infected host. The morphological and antigenic differences of these parasites in the course of their life cycles in man make it possible to define at least four distinct stages of development.

The very first stage of development of the parasite in man corresponds to the sporozoite form introduced into the blood of the host by bites of insect carriers of the parasite. The second stage corresponds to the passage of the parasite into the liver and to the infection of the hepatic cells in which the parasites develop to form the hepatic schizonts which release the hepatic merozoites as a result of bursting. The third stage is characterized by the infection of the blood erythrocytes by the asexual forms (merozoites) of the parasite; this erythrocytic stage of development of the parasite corresponds to the pathogenic phase of the disease. The fourth stage corresponds to the formation of sexual forms (or gametocytes) which will become the extra-cellular gametes in the mosquito.

It is known that numerous studies have been undertaken to isolate from strains of parasites which are infectious for a human host polypeptide fractions in order to provide an in vitro diagnosis of malaria by detection of the corresponding antibodies, on the one hand, and in order to attempt to vaccinate against malaria, on the other.

For example, banks of cloned cDNAs derived from the sporozoites of *Plasmodium falciparum* have been established by ENEA et al. (1984) Science, vol. 225, 628–630. It was recognized that these banks comprised clones likely to express immunogenic polypeptides containing repetitive units of 4 amino acids specific for the circumsporozoite antigen (of *P. falciparum*).

However, little work has been carried out on the hepatic forms of the parasites responsible for malaria. The morphology of the hepatic forms was described for the first time in 1948 on the basis of biopsies on infected human volunteers (Trans. Roy. Soc. Trop. Med. Hyg., 41, 785 (1984)). It was possible to describe a specific antigen of the hepatic stage of *P. falciparum* in the liver of South American monkeys insensitive to the blood forms of the parasite but in which the hepatic forms can develop (Am. J. Trop. Med. Hyg., 33, (3) 336–341 (1984)).

The detection of the localization of the specific antigen(s) of the liver (hereafter designated by LSA for "Liver Specific Antigen") was carried out by means of immunofluorescence throughout the stages of maturation of the schizont. It is localized at the periphery of the parasite 5 to 40 microns in size; subsequently, it is distributed between the cytomeres or bundles of merozoites when the schizonts attain between 50 and 100 microns. It is distinct from the surface antigens of the sporozoites and the antigen shared by the schizonts of the blood and the liver which give an immunofluorescent image in the interior of the parasite.

Although it is henceforth possible to cultivate the hepatic forms of *P. falciparum* in human hepatocytes (Science, 227, 440 (1985)), the low yield of mature forms of the parasite by the in vitro and in vivo methods of culture does not permit biochemical analysis of the antigen produced at the hepatic stage.

It has also been observed that individuals suffering from malaria possess a very high level of antibodies directed against the LSA. The LSA seems to be a very powerful immunogen, among the most powerful of all the antigens synthesized at the various stages of development of the parasite. On the other hand, the level of antibodies directed against the forms of the blood stages of the parasite is sometimes very low, and consequently the diagnosis carried out on the basis of antigens specific for the blood stages can sometimes be falsely negative.

One of the aims of the present invention is precisely that of making possible the in vitro diagnosis of the infection of an individual by *P. falciparum* under conditions more sensitive than the present methods allow.

Another subject of the invention is novel compositions for the vaccination of humans against the malaria caused by *P. falciparum.*

The invention relates more particularly to molecules, or peptide or polypeptide compositions, characterized by the presence of their structure of one or more peptide sequences carrying one or more epitopes characteristic of the protein resulting from the infectious activity of *P. falciparum* in hepatic cells, in particular the epitope B.

A polypeptide composition according to the invention is characterised essentially by the presence of a sequence of 17 amino acids of formula:

Leu-Ala-Lys-Glu-Lys-Leu-Gln-X-Gln-Gln-Ser-Asp-Leu-Glu-Gln-Glu-Arg in which:

X is Glu or Gly and in which "Leu" is leucine, "Ser" is serine, "Lys" is lysine, "Glu" is glutamic acid, "Gln" is glutamine, "Asp" is aspartic acid, and "Arg" is arginine. When X is "Glu", the corresponding peptide will be designated in the remainder of this text as "peptide I", and when X is "Gly" as "peptide II".

In the first instance, the invention relates to synthetic monomeric peptides comprising a unique peptide sequence of 17 amino acids corresponding to the above-mentioned formula, and the terminal amino acids of which possess, respectively, free amino and carboxylic termini, or oligomers containing in particular multiples of any one of the two peptide sequences I and II of 17 amino acids mentioned above.

It is obvious that free reactive functions which certain amino acids entering into the composition of the molecules according to the invention are likely to possess, in particular the free carboxyl groups carried by the Glu residues and by the C-terminal amino acid, on the one hand, and/or the free groups carried by the N-terminal amino acid or by amino acids within the peptide chain, for example Lys, on the other hand, may be modified provided that this modification does not lead to an alteration of the antigenic, and possibly immunogenic, properties of the whole molecule. The molecules thus modified naturally enter into the framework of the protection given to the invention by the claims. These carboxyl functions are possibly acylated or esterified.

Other modifications also enter into the framework of the invention. In particular, amine or ester functions, or both at once, of the terminal amino acids may themselves be engaged in linkages with other amino acids. For example, the N-terminal amino acid may be linked to a sequence comprising one to several amino acids corresponding to a part of the C-terminal region of another peptide conforming to the definition which was given above, or vice versa.

It will also be obvious that any peptide sequence resulting from the modification, by substitution and/or by addition and/or suppression of one or more amino acids, of one or other of the 2 peptide sequences I and II of 17 amino acids enters into the framework of the protection given to the invention by the claims, provided that this modification does not alter the antigenic or immunogenic properties of the polypeptides I and II, in particular when these immunogenic properties have been suitably reinforced, for example by combination of these polypeptides I or II with an appropriate immunological adjuvant (for example a muramylpeptide) or by coupling with a carrier molecule of higher molecular weight (for example a serum albumin or a poly-lysine) or a toxin of the tetanus type or another antigen of *P. falciparum*.

More generally, the invention relates to any molecule characterized by the presence in its structure of one or more peptide sequences exhibiting immunological cross-reactions with the two peptide sequences corresponding to the preceding formula with respect to the antibodies inducible by these latter in vivo.

The invention also relates to any peptide, the structure of which is derived from those which have been indicated previously by permutation of one or more amino acids. In particular, it also relates to peptides of formula:

Ala-Lys-Glu-Lys-Leu-Gln-X-Gln-Gln-Ser-Asp-Leu-Glu-Gln-Glu-Arg-Leu

Lys-Glu-Lys-Leu-Gln-X-Gln-Gln-Ser-Asp-Leu-Glu-Gln-Glu-Arg-Leu-Ala

Glu-Lys-Leu-Gln-X-Gln-Gln-Ser-Asp-Leu-Glu-Gln-Glu-Arg-Leu-Ala-Lys

Lys-Leu-Gln-X-Gln-Gln-Ser-Asp-Leu-Glu-Gln-Glu-Arg-Leu-Ala-Lys-Glu

Leu-Gln-X-Gln-Gln-Ser-Asp-Leu-Glu-Gln-Glu-Arg-Leu-Ala-Lys-Glu-Lys

Gln-X-Gln-Gln-Ser-Asp-Leu-Glu-Gln-Glu-Arg-Leu-Ala-Lys-Glu-Lys-Leu

X-Gln-Gln-Ser-Asp-Leu-Glu-Gln-Glu-Arg-Leu-Ala-Lys-Glu-Lys-Leu-Gln

Gln-Gln-Ser-Asp-Leu-Glu-Gln-Glu-Arg-Leu-Ala-Lys-Glu-Lys-Leu-Gln-X

Gln-Ser-Asp-Leu-Glu-Gln-Glu-Arg-Leu-Ala-Lys-Glu-Lys-Leu-Gln-X-Gln

Ser-Asp-Leu-Glu-Gln-Glu-Arg-Leu-Ala-Lys-Glu-Lys-Leu-Gln-X-Gln-Gln-

Asp-Leu-Glu-Gln-Glu-Arg-Leu-Ala-Lys-Glu-Lys-Leu-Gln-X-Gln-Gln-Ser-

Leu-Glu-Gln-Glu-Arg-Leu-Ala-Lys-Glu-Lys-Leu-Gln-X-Gln-Gln-Ser-Asp

Glu-Gln-Glu-Arg-Leu-Ala-Lys-Glu-Lys-Leu-Gln-X-Gln-Gln-Ser-Asp-Leu

Gln-Glu-Arg-Leu-Ala-Lys-Glu-Lys-Leu-Gln-X-Gln-Gln-Ser-Asp-Leu-Glu

Glu-Arg-Leu-Ala-Lys-Glu-Lys-Leu-Gln-X-Gln-Gln-Ser-Asp-Leu-Glu-Gln

Arg-Leu-Ala-Lys-Glu-Lys-Leu-Gln-X-Gln-Gln-Ser-Asp-Leu-Glu-Gln-Leu in which X has the meaning indicated above.

As in the case of the first peptide defined above, these various peptides which have just been named can be modified without at the same time departing from the framework of the invention, provided that these modifications of structure do not lead to profound alterations of their antigenic properties.

The peptides according to the invention can be prepared by the standard methods used in the field of the synthesis of peptides. Synthesis can be carried out in homogeneous solution or on a solid phase.

For example, recourse may be had to the method of synthesis in homogeneous solution described by HOUBEN-WEYL in the monograph entitled "Methoden der Organischen Chemie" (Methods in Organic Chemistry) edited by E. Wunsch, vol. 15-I and II., THIEME, Stuttgart 1974.

This method of synthesis consists of condensing successive amino acids two at a time in the required order, or of condensing amino acids with fragments already formed and already containing several amino acids in the appropriate order or also of condensing several fragments previously prepared in this way, it being understood that precautions will be taken to protect beforehand all the reactive functions presented by these amino acids or fragments with the exception of the amino function of one and the carboxyl function of the other which must be free to enter into the formation of the peptides bond, particularly after activation of the carboxyl function according to the well-known methods of peptide synthesis. As an alternative, recourse may be had to coupling reactions which make use of standard coupling reagents of the carbodiimide type such as, for example, 1-ethyl-3-(3-dimethyl-aminopropyl)-carbodiimide. When the amino acid used possesses an additional acidic function (particularly in the case of glutamic acid) such functions must be protected, by t-butyl ester groups, for example.

In the case of step-wise synthesis in which one amino acid is added at a time, the synthesis starts preferably with the condensation of the C-terminal amino acid with the amino acid which corresponds to the neighboring amino acid in the desired sequence and it continues in this manner until the N-terminal amino acid is reached. According to another preferred method of the invention use may be made of the procedure described by R. D. MERRIFIELD in the article entitled "Solid phase peptide synthesis" (J. Am. Chem. Soc., 45, 2149–2154).

In order to prepare a peptide chain according to the procedure of MERRIFIELD, it is necessary to make use of a very porous polymeric resin to which is attached the first amino acid, the C-terminal residue of the chain. This amino acid is attached to the resin through its carboxyl group and its amino function is protected by the t-butoxycarbonyl group, for example.

When the C-terminal amino acid is thus attached to the resin as the first amino acid, the protecting group of the amine function is removed by washing the resin with an acid. In the case in which the protecting group of the amine function is the t-butoxycarbonyl group, it can be removed by treatment of the resin with trifluoroacetic acid.

Subsequently, the second amino acid, which furnishes the second amino acid of the desired sequence counting from the C-terminal amino acid residue, is coupled to the deprotected amino function of the C-terminal amino acid, the first amino acid attached to the resin. The carboxyl function of this second amino acid is activated preferably for example with dicyclohexylcarbodiimide and its amine function is protected for example by means of the t-butyloxycarbonyl group.

In this way, the first part of the desired peptide chain is obtained consisting of two amino acids, the terminal amine function of which is protected. The amine function is deprotected as previously described and subsequently the third amino acid is coupled under conditions analagous to those used for the addition of the second C-terminal amino acid.

In this way, each of the amino acids which will constitute the peptide chain is coupled one after the other to the deprotected amine group of the portion of the peptide chain already formed and which is attached to the resin.

When the desired peptide chain has been assembled in its entirety, the protecting groups of the different amine acids constituting the peptide chain are removed and the peptide is cleaved from the resin by means of hydrogen fluoride, for example.

The invention also relates to water-soluble oligomers of the above-mentions peptide monomers. Oligomerization can bring about an increase in the immunogenicity of the peptide monomers according to the invention. It may be mentioned that these oligomers may, for example, contain from 2 to 10 monomeric units without implying that this number is to be considered as limiting.

The monomeric units forming this oligomer are either all constituted of the polypeptide of sequence I or by the polypeptide of sequence II or by both of these polypeptides.

For the preparation of the oligomer use may be made of any method of polymerization commonly used in the field of peptides, this polymerization reaction being continued until an oligomer or a polymer is obtained which contains the number of monomeric units required for the acquisition of the desired immunogenicity.

One method of oligomerization or polymerization of the monomer consists in allowing the latter to react with the cross-linking agent such as glutaraldehyde.

Use may also be made of other methods of oligomerization or coupling, for example that involving successive coupling of monomeric units through their terminal carboxyl and amine functions in the presence of homo- or heterobifunctional coupling agents.

For the production of molecules containing one or more sequences of 17 amino acids such as those defined above, use may also be made of genetic engineering techniques using micro-organisms transformed by a specific nucleic acid containing the corresponding, appropriate nucleotide sequences.

The invention therefore also relates to nucleic acids containing one or more of these repetitive sequences each comprising 17 triplets of the type indicated above.

The invention also relates to the conjugates obtained by covalently coupling the peptides according to the invention (or the above-mentioned oligomers) to carrier molecules (naturally occurring or synthetic), physiologically acceptable and non-toxic, through the intermediary of complementary reactive groupings situated on the carrier molecule and the peptide. Examples of appropriate groupings are illustrated in what follows.

As examples of carrier molecules or macromolecular supports constituting part of the conjugates according to the invention, mention will be made of naturally occurring proteins such as tetanus toxoid, ovalbumin, serum albumins, hemocyanins, etc.

As examples of synthetic macromolecular supports mention may be made of the polylysines or poly(D.L.-alanine)-poly(L-lysine).

Other types of macromolecular supports which can be used are mentioned in the literature; usually they have a molecular weight higher than 20,000.

In order to synthesize the conjugates according to the invention use may be made of known procedures such as that described by FRANTZ and ROBERTSON in Infect. and Immunity, 33, 193–198 (1981) or that described in Applied and Environmental Microbiology (October 1981), vol. 42, No. 4, 611–614 by P. E. KAUFFMAN by using the peptide and the appropriate carrier molecule.

In practice, and without implying any restriction on the use of others, it is advantageous to use the following compounds as coupling agents: glutaraldehyde, ethyl chloroformate, water-soluble carbodiimides [N-ethyl-N'(3-dimethylamino-propyl) carbodiimide, HCl], diisocyanates, bisdiazobenzidine, di- and trichloro-s-triazines, cyanogen bromide as well as the coupling agents mentioned in Scand. J. Immunol., (1978), vol. 8, p. 7–23 (AVRAMEAS, TERNYNCK, GUESDON).

It is possible to use any other coupling procedure which causes one or more reactive functions of the peptide, on the one hand, to react with one or more reactive functions of the support molecules on the other. Advantageously, these reactive functions are carboxyl and amine functions which can undergo a coupling reaction in the presence of a coupling agent of the type used in the synthesis of proteins, for example, 1-ethyl-3-(3-dimethylamino-propyl)-carbodiimide, N-hydroxybenzotriazole, etc. Use may again be made of glutaraldehyde, particularly when it is required to link amino groups to each other which are situated on the peptide and the support molecule, respectively.

A group of preferred molecules according to the invention is constituted by those possessing an α-helical confirmation, this latter reinforcing the antigenic and immunogenic properties of the said molecules. Such molecules possessing an α-helical confirmation have been detected by circular dichroism in trifluoroethanol or in aqueous solution.

The molecules according to the invention possess antigenic properties characteristic of the specific LSA antigen of the hepatic stage of development of P. falciparum.

Indeed, as will be described more particularly with the aid of examples of molecules according to the invention in the detailed description which follows, the molecules according to the invention react specifically with the antibodies directed against the LSA antigen produced by P. falciparum, but not with the antibodies directed against other antigens produced by P. falciparum or against antigens produced by other species of Plasmodium.

These molecules according to the invention thus recognise specifically the antibodies produced by the immune system under the effect of the LSA antigen of an individual infected by P. falciparum, the highly immunogenic character of which has already been mentioned.

Thus, the possibility of producing in large amounts molecules according to the invention as well as their properties of specific recognition of the antibodies most actively produced at the time the infection of an individual by P. falciparum make the said molecules reagents of choice for the in vitro diagnosis of malaria in an individual infected by P. falciparum.

Thus, the invention relates to a procedure for the in vitro detection of antibodies which can be correlated with the malaria resulting from the infection of an individual by P. falciparum in a tissue or biological fluid likely to contain them, this procedure comprising the placing in contact of this tissue of biological fluid with a molecule according to the invention under conditions which allow an immunological reaction in vitro between the said molecules and the antibodies possibly present in the tissue or biological fluid, and in the in vitro detection of the antigen-antibody complex which may possibly be formed.

The biological medium is preferably constituted by a human serum.

Any standard procedure may be used to carry out such detection.

As an example, a preferred method involves immunoenzymatic processes according to the ELISA technique, or immunofluorescent processes, or radioimmunological processes (RIA) or equivalent processes.

Thus, the invention also relates to any molecule according to the invention labelled with the aid of a suitable marker of the enzymatic, fluorescent, radioactive, etc. . . . type.

Such methods comprise for example the following steps:

deposition of defined amounts of a polypeptide composition according to the invention in the wells of a microtiter plate, introduction into the said wells of increasing dilutions of the serum requiring diagnosis, incubation of the microtiter plate, repeated rinsing of the microtiter plate, introduction into the wells of the microtiter plate of labelled antibodies against immunoglobulins of the blood, the labelling of the antibodies having been carried out with the aid of an enzyme chosen from among those which are capable of hydrolyzing a substrate, and of modifying the absorption of radiation of this latter, at at least one specific wavelength, detection of the amount of substrate hydrolyzed in comparison with a control.

The invention also relates to kits for the in vitro diagnosis of malaria caused by *P. falciparum* which contain:

a polypeptide composition according to the invention, the reagents for constituting the medium appropriate for carrying out the immunological reaction, the reagents used to detect the antigen-antibody complex produced by the immunological reaction. These reagents may also bear a marker or be capable of being recognized in turn by a labelled reagent, more particularly in the case in which the above-mentioned polypeptide composition is not labelled.

a reference biological tissue fluid not containing antibodies recognized by the above-mentioned polypeptide composition.

The invention relates to the antibodies themselves formed against the peptides of the invention.

It will be obvious that these antibodies are not limited to polyclonal antibodies.

The invention also relates to any monoclonal antibody produced by any hybridoma capable of being formed by standard methods from the spleen cells of an animal, in particular of a mouse or a rat immunized against one of the peptides of the invention, on the one hand, and the cells of an appropriates myeloma cell line on the other, and the being selected by its capacity to produce monoclonal antibodies recognizing the polypeptide initially used for the immunization of the animals, i.e. more particularly the polypeptide I or the polypeptide II.

Finally, the invention opens the route to the development of new principles of vaccination against malaria resulting from the infection of an individual by *P. falciparum*.

The invention also relates to the compositions prepared in the form of vaccines containing either the peptide according to the invention or an oligomer of this peptide or also a conjugate of this peptide or oligomer with a carrier molecule, in combination with an appropriate pharmaceutically acceptable vehicle and, if necessary, with other active principles of vaccination against malaria.

Advantageous pharmaceutical compositions are constituted by solutions, suspensions or injectable liposomes containing an efficacious dose of at least one product according to the invention. These solutions, suspensions and liposomes are preferably prepared in a sterilized isotonic aqueous phase, preferably saline or a glucose solution.

The invention relates more particularly to those suspensions, solutions and liposomes which are suitable for administration by intradermal, intramuscular and subcutaneous injections or also by scarifications.

The invention also relates to pharmaceutical compositions which can be administered by other routes, in particular by the oral or rectal route, or also in the form of aerosols intended to come into contact with mucous membranes, in particular ocular, nasal, pulmonary and vaginal mucous membranes.

Consequently, it relates to pharmaceutical compositions in which at least one of the products according to the invention is combined with solid or liquid, pharmaceutically acceptable excipients, suited to the making up of oral, ocular or nasal forms, or with excipients suited to the making up of forms for rectal administration, or also with gelatinous excipients for vaginal administration. It also relates to isotonic liquid compositions containing at least one of the conjugates according to the invention, suited to administration to the mucous membranes, in particular ocular and nasal membranes.

Advantageously, the vaccinal compositions according to the invention contain in addition a vehicle such as polyvinylpyrrolidone which facilitates the administration of the vaccine. Instead of polyviny-pyrrolidone it is possible to use any other type of adjuvant in the classical sense which was formerly attributed to this expression, i.e. a substance allowing the more ready absorption of a medicine or facilitating its action in the organism. As examples of other adjuvants of this latter type, mention should also be made of carboxymethyl-cellulose, the hydroxides and phosphates of aluminium or all other adjuvants of this type well known to the person skilled in the art. Finally, they contain, if necessary, an immunological adjuvant, in particular of the muramylpeptide type.

The invention is obviously not limited to the embodiments described above as examples and the person skilled in the art can make modifications to it without in any way departing from the framework of the claims made below; in particular, some of the amino acids occurring in the sequence of the peptides according to the invention can be replaced by isofunctional or isosteric amino acids; for example, one or more of the following substitutions can be envisaged:

Glu is substituted by Asp or Gln,

Leu is replaced by Ala, etc.

It is of course understood that the peptides which result from such substitutions consist of equivalents of the peptides more especially claimed, provided that they themselves or oligomers or conjugates formed from these peptides exhibit similar immunogenic properties.

The invention also relates more particularly to the "chimeric proteins" which may be obtained by the techniques of genetic engineering, such chimeric proteins containing one or more peptide sequences containing respectively the 17 amino acids of the sequences of the invention, and incorporated into or attached to a peptide fragment other than the β-galactosidase. This latter peptide fragment preferably has a molecular weight sufficient to reinforce the immunogenicity of the peptide sequences according to the invention and does not interfere from an immunological point of view with the manifestation of the desired immunogenicity.

In the course of the description which follows, additional characteristics of the invention will become apparent of the conditions under which a polypeptide containing a multiplicity of sequences of 17 amino acids according to the invention was obtained.

Reference will be made in what follows to the figures in which

FIG. 1 provides the nucleotide sequence of one of the recombinant nucleic acids studied (clone DG 307) which itself contains a specific sequence coding for a polypeptide characteristic of the hepatic forms of P. falciparum;

FIG. 2 provides the sequence of amino acids encoded in the above-mentioned specific nucleotide sequence.

Sera obtained from European individuals living in endemic zones and following a sustained prophylaxis with medicines directed against the schizonts of the blood stages have been selected and tested by using antigens of the sporozoite stage (CS antigens), the hepatic stage (LSA antigen) and the blood stages. The majority of these sera react with the antigens of all the stages probably because prophylaxis was interrupted. Three sera taken from individuals having lived in rural tropical Africa and having ingested 100 μg of chloroquine per day without interruption for 23 to 26 years did not react with the antigens of the blood stages according to the immunofluorescence assay (IFA). These three sera possessing, however, high titres of antibodies directed against the sporozoites and the LSA proteins (IFA dilution 1/3200 and 1/6400, respectively).

One of the three preceding sera, of reduced specificity, was used to screen for a bank of genomic DNA constructed in the bacteriophage λgt 11 in the following manner:

1) CONSTRUCTION OF THE BANK OF GENOMIC DNA OF *Plasmodium falciparum.*

The genomic DNA of the clone 96 of the Thai strain Tak9 of *P. falciparum* (Science, 212, 1.37–1.38 (1981)) was isolated by the standard techniques.

Samples of 18 μg of DNA of *P. falciparum* were incubated at 15° C. in 50 mM Tris HCl buffer, pH 7.5, 1 mM $MnCl_2$, 20 μg/ml of bovine serum albumen with amounts of DNAase I (Boehringer Mannheim) of 5 pg for 5 minutes or 3.5 pg for 5 or 10 minutes. After addition of 5 mM EDTA (ethylenediamine tetracetic acid), the samples of DNA were cooled and purified by extraction with the mixture phenol/chloroform/isoamyl alcohol (25 V/24 V/1 V), then with ether. The DNA is concentrated by precipitation with ethanol at −20° C. in the presence of 2.5M ammonium acetate.

45 μg of DNA thus treated were methylated by 180 U of Eco R1 methylase (Biolabs) under the conditions recommended by the supplier, with the further addition of 5 mM DTT (dithiothreitol), for 15 minutes at 37° C. After purification of the DNA as above, 10 μg of DNA were incubated with 40 mM Tris HCl pH 8.0, 10 mM ammonium sulfate, 10 mM 2-mercaptoethanol, 0.5 mM EDTA, 0.05 mM NAD (nicotinamide adenine dinucleotide) 0.1 mM dXTP (comprising the 4 deoxynucleotide triphosphates dATP, dCTP, dGTP and dTTP), in the presence of 10 U T4 DNA polymerase (PL Biochemicals) and of 10 U of *E. coli* DNA ligase (Biolabs). The DNA was purified and concentrated as above.

8 μg of DNA were then ligated with 0.4 μg of an Eco R1 adaptor or "linker" (Eco R1 phosphorylated adaptors marketed by Biolabs) by means of 4 U T4 DNA ligase (Biotec) in 50 mM Tris HCl buffer, pH 8.0, 10 mM $MgCl_2$, 20 mM DTT, 1 mM ATP, 50 μg/ml bovine serum albumen.

After incubation at 4° C. for 5 hours, 2 U T4 DNA ligase are added and the reaction is continued at 4° C. for 16 hours. The tube is then subjected to several cycles of freezing to −80° C./thawing in order to stop the reaction. The DNA is then diluted and the incubation buffer adjusted so as to give rise to the conditions recommended by the supplier for the use of the Eco R1 enzyme. 100 U of Eco R1 enzyme (Promega Biotec) are added and incubated for 3 hours at 37° C. The reaction is stopped by heating for 10 minutes at 60° C., and the DNA is purified and concentrated as above.

The DNA is resuspended in 100 μl of 50 mM Tris HCl buffer, pH 8.0, 1 mM EDTA, and placed on a 5–20% sucrose gradient prepared in 25 mM sodium acetate, 10 mM EDTA and centrifuged in the Beckman SW 50.1 rotor at 45,000 revolutions per minute for 150 minutes. The fractions are analyzed on agarose gel and those which contain fragments of DNA of sizes varying between about 300 pb and 2,500 bp are pooled and dialyzed against the 50 mM Tris HCl buffer, pH 8.0, 1 mM EDTA at 4° C. The DNA is concentrated by a precipitation with ethanol. About 400 ng of this DNA were ligated to 1 μg of DNA of the vector gt 11 (Proc. Natl. Acad. Sci., USA, 80, 1194–1198 (1983)) cut by Eco R1 and dephosphorylated (Protoclone of Promega Biotec), in a volume of 10 μl (of 50 mM Tris HCl buffer, pH 8.0, 10 mM $MgCl_2$, 20 mM DTT, 1 mM ATP, 50 μg/ml bovine serum albumin) by means of 1 U T4 DNA ligase (Biotec).

The products of ligation were encapsidated in vitro in the *E. coli* extracts prepared from the bacterial strains constructed by B. Hohn (Methods Enzymol. 68, 299), according to the technique described by Maniatis et al (Molecular Cloning, a laboratory manual, p. 264, Cold Spring Harbor Laboratory (1982)). About 7 millions of recombinant bacteriophages were obtained.

2) IMMUNOLOGICAL SCREENING OF THE BANK

The recombinant bacteriophages were spread on a culture medium containing the indicator bacterium Y 1090 at a density of 50,000 plaques per 90 mm Petri dish, and incubated at 42° C. for 3 hours. A nitrocellulose filter (Schleicher and Schuell, BA 85) saturated with 0.01M IPTG isopropyl-β-thiogalactopyranoside (Sigma) is placed on the dishes which are incubated at 37° C. for 3 hours. On the completion of these incubations, the nitrocellulose filters are removed and the Petri dishes are stored at 4° C.

The nitrocellulose filters are placed in a bath of TL buffer: 50 mM Tris HCl, pH 8.0, 150 mM NaCl, 5% skimmed milk, 0.05% Tween 20 (Sigma). The filters are incubated for 15 hours at 4° C. in TL buffer, then twice for 15 minutes at 20° C. They are then incubated for 1 hour with a pool of immune human antisera directed against the antigens of all the stages of development of *P. falciparum,* treated beforehand in order to deplete it of anti-*E. coli* antibodies according to the technique described by Ozaki et al (J. Immunol. Methods, 89, 213–219, 1986). The pool of human antisera was used at a dilution of 1/200 in TL buffer. The inculbation was done at 20° C. for 1 hour. The filters were washed 4 times with the TL buffer, then incubated with human anti-immunoglobulin antibodies conjugated to horseradish peroxidase (Biosys) and iodinated with $^{125}$I iodine for 1 hour at 20° C. After several washes in TL buffer, then in 50 mM Tris HCl buffer, pH 8.0, 150 mM NaCl, the enzymatic activity of the peroxidase is revealed (Ozaki et al, previously cited), the filters are dried in air and autoradiographed on Kodak Royal X-OMat AR film with an amplifying screen.

A collection of about 1200 clones of recombinant bacteriophages was constituted by sampling the plaques of lysis corresponding to the positive signals. These clones were then subjected to a second cycle of immunological screening, this time by employing one of the 3 human sera previously described (p. 14) and possessing no or few antibodies directed against the erythrocytic forms of *P. falciparum* and a high titre against the hepatic forms of the parasite. This immunological screening was carried out according to the protocol described above. This serum reacts with only 15% of the producer clones of a specific antigen of *P. falciparum* (60 out of 400 tested) and 22 of the most active clones were selected and characterized as follows.

The human antibodies which react with the antigenic determinants expressed by the recombinant clones were purified by affinity on the recombinant proteins according to the technique described by Ozaki et al (previously cited). These specific antibodies were incubated with preparations of parasites at different stages of development (sporozoite, hepatic stage or erythrocytic stages), and the reaction was studied by indirect immunofluorescence. The recombinant clones on which antibodies specific for the hepatic stage are retained by affinity and hence which express determinants specific for this stage, were studied; they are the clones DG 307, DG 199 and DG 145. These specific antibodies of these 3 clones react specifically with the hepatic schizonts such as may be produced after infection of human or monkey hepatocytes by sporozoites of *P. falciparum*; the localization of the fluorescence was determined as being identical with that considered characteristic of LSA.

The species and stage-specificity of the 3 clones in DG 145, DG 199 and DG 307 was tested in the following manner. Firstly, it was established that the same antibodies purified by affinity and which react in IFA (or which are IFA positives) with LSA do not react with preparations of dried or moist sporozoites, nor with the antigens of the blood stages, whether they are assayed by IFA with parasites fixed with acetone or by immunoblotting by utilising proteins of all of the stages extracted with SDS. The antibodies purified by affinity do not react with the antigens of the hepatic stage of *P. yoelii*, nor with the hepatic schizonts of *P. vivax* prepared from *Saimiri sciureus* monkeys.

Secondly, the recombinant proteins of DG 145, DG 199 and DG 307 do not react with the sera obtained from 2 patients suffering from malaria (malaria caused by *P. falciparum*) as a result of accidental transfusion and which, by definition, thus do not have antibodies against the specific antigens of the earlier stages (sporozoites and antigens of the hepatic stage). These proteins do not react with 2 monoclonal antibodies recognizing the CS tetrapeptide, with the sera of mice immunized with the recombinant CS antigens R32t and 32 (Science, 228, 958 (1985)). Furthermore, the recombinant protein did not react with human antisera directed against *P. vivax* (although the sera were positive with the hepatic schizonts of *P. vivax*), *P. ovale* and *P. cynomolgi* (Ann. Soc. Belg. Med. Trop., 60, 348 (1980)) when these are assayed by the technique of immunodot blots whereas they are positive with all of the anti-*P. falciparum* human sera assay.

The stability to heat, known as being a characteristic of the mature LSA (Ann. J. Trop. Med. Hyg., 33 (3) 336–341 (1984)) was also demonstrated for the fusion protein produced by the clone DG 307. It remains antigenically active after a treatment for 15 minutes at 100° C. For this reason the clone DG 307 was analyzed in more detail.

The insert of 196 base pairs of *P. falciparum* was purified and recloned within the plasmid pUC13 and bacteriophage M13 mp 8 (Nucleic Acids Research, 9, 309–321 (1981)). The DNA sequence and the genomic organization of the LSA gene were then determined. FIG. 1 shows that the clone DG 307 contains a DNA fragment composed entirely of repetition of a sequence of 51 base pairs.

Only one reading frame is in phase with the lac Z gene of the β-galactosidase, an expected property since the clone produces a fusion protein which carries the isotopes recognized by human serum. The sequence of amino acids corresponding to this fragment is represented in FIG. 2. It is composed of a repetition of 17 amino acids rich in glutamine, glutamic acid and leucine. Computer analysis of this sequence indicates that it had a high possibility of possessing an α helical structure without β bends. In addition, no homology between the presently known DNA sequences and the DNA sequence coding for the said protein had been detected by analysis of the Los Alamos and NBRF data banks. This is in agreement with the specificity of the hepatic stage of the LSA protein.

Analyses by blotting according to the method of Southern using the fragment of 196 base pairs cloned in pUC 13 show that this fragment is a derivative of a unique gene since it hybridizes with unique Eco RI (6.5 kb) and Dra I (4.5 kb) fragments. The gene seems to be polymorphic since Rsa I fragments of different sizes were observed when the DNA derived from one of the strains was used. The gene was found in all strains of *P. falciparum* examined up to now, localized on one of the larger chromosomes. The DNA hybridization studies show that the 3 clones DG 307, DG 145 and DG 199 are distinct fragments derived from the same gene.

The type of repetition encoded in DG 307 seems to be conserved and implies that the corresponding epitope(s) may be present in all strains of *P. falciparum*. This is in agreement with the observation of the fact that the gene which is derived from the Thai strain Tak9.96 was detected by using African human serum or serum of persons immunized by African strains.

As the repetitive epitopes appear to be general characteristic of the antigens of *P. falciparum* (Nature, 306, 751–756 (1983); Nature, 311, 382–385 (1984); Science, 225, 593–599 (1984); Science, 227, 1595–1597 (1985); Cell 40, 775–783 (1985)), it is not surprising that the LSA which is highly immunogenic in man, also possesses repetitive structures. The strong reaction of the clone DG 307 with the human antisera indicates that the natural epitope is defined by less than 4 repetitions.

The relation between the epitope(s) expressed by the recombinant protein of DG 307 and the epitopes present in the mature protein of the hepatic stage was studied in the following manner: 10 human sera coming from the Ivory Coast, Gabon and Zaire, possessing high titres of antibodies directed against the said mature protein, were adjusted to dilutions exhibiting a marked positive IFA reaction with the antigens of the hepatic stage. Subsequently, these sera were incubated either in the presence of a protein extract of the clone DG 307 induced by IPTG or with proteins derived from 2 other clones expressing antigenic determinants of the blood stages. The concentrations of the antigens were adjusted to a level of reactivity similar to the preceding one by assaying several dilutions by immunodot blots and by revealing the bound antibody by using a pool of hyperimmune sera. After incubation of 2 hours at ambient temperature, the specificity for the hepatic schizonts of the different solutions was assayed by IFA. The results show that the antibodies preincubated with the extract from DG 307 no longer had any IFA reactivity, whereas those incubated with the other two extracts did not show their activity against the hepatic antigen to be diminished.

It thus seems that the DG 307 codes for the principal epitope of the LSA since in these absorption experiments, the IFA reactivity to the mature protein was abolished for 9 of the 10 human sera assayed, whereas no diminution of IFA activity was observed after preincubation of the same 10 sera in the presence of recombinant proteins different from those of DG 307.

The invention also relates to the recombinant nucleic acids containing at least one of the polypeptide sequences I or II or both at once, as well as the micro-organisms, in particular the E. coli bacteria transformed by these recombinant nucleic acids and capable of expressing the said polypeptides.

The invention relates to these sequences of nucleic acids or to equivalent sequences which can be synthesized and which code for the same amino acids.

It will be immediately apparent to the person skilled in the art that in these sequences certain of the nucleotides may be replaced by others on account of the degeneracy of the genetic code without the peptides coded being modified. All of these nucleotide sequences as well as those which code for polypeptides which differ from the preceding ones by one or more amino acids without their intrinsic immunogenic activity being modified in a similar manner form part of the invention. Naturally, it is the same for nucleotide sequences which can be reconstituted and which are capable of coding for oligomers such as those which were defined above. The monomeric sequences are linked directly end to end or by the intermediary of peptide sequences without effect on the immunogenic properties of the oligomers so formed.

Finally, the invention relates to the vectors modified by these micro-organisms, these vectors being naturally provided with regulation and termination preceding and following the above-mentioned nucleic acid sequences which make possible the expression of these latter in competent cellular organisms.

Of the nucleotide sequences which code for the characteristic peptides which have been defined above, mention should be made of those which are characterized by the triplet sequences which follow, these sequences corresponding in particular in the case of the first three to peptide I and in the case of the last one to peptide II, the formulae of which have been indicated earlier (it being understood that the nucleotides which are replaced by dots in the sequences below are identical with those of the first sequence directly above them).

Leu-Ala-Lys-Glu-Lys-Leu-Gln-Glu-Gln-Gln-Ser-Asp-Leu-Glu-Gln-Glu-Arg

Ala-Lys-Glu-Lys-Leu-Gln-Glu-Gln-Gln-Ser-Asp-Leu-Glu-Gln-Glu-Arg-Leu

Lys-Glu-Lys-Leu-Gln-Glu-Gln-Gln-Ser-Asp-Leu-Glu-Gln-Glu-Arg-Leu-Ala

Glu-Lys-Leu-Gln-Glu-Gln-Gln-Ser-Asp-Leu-Glu-Gln-Glu-Arg-Leu-Ala-Lys

Lys-Leu-Gln-Glu-Gln-Gln-Ser-Asp-Leu-Glu-Gln-Glu-Arg-Leu-Ala-Lys-Glu

Leu-Gln-Glu-Gln-Gln-Ser-Asp-Leu-Glu-Gln-Glu-Arg-Leu-Ala-Lys-Glu-Lys

Gln-Glu-Gln-Gln-Ser-Asp-Leu-Glu-Gln-Glu-Arg-Leu-Ala-Lys-Glu-Lys-Leu

Glu-Gln-Gln-Ser-Asp-Leu-Glu-Gln-Glu-Arg-Leu-Ala-Lys-Glu-Lys-Leu-Gln

Gln-Gln-Ser-Asp-Leu-Glu-Gln-Glu-Arg-Leu-Ala-Lys-Glu-Lys-Leu-Gln-Glu

Gln-Ser-Asp-Leu-Glu-Gln-Glu-Arg-Leu-Ala-Lys-Glu-Lys-Leu-Gln-Glu-Gln

Ser-Asp-Leu-Glu-Gln-Glu-Arg-Leu-Ala-Lys-Glu-Lys-Leu-Gln-Glu-Gln-Gln

Asp-Leu-Glu-Gln-Glu-Arg-Leu-Ala-Lys-Glu-Lys-Leu-Gln-Glu-Gln-Gln-Ser

Leu-Glu-Gln-Glu-Arg-Leu-Ala-Lys-Glu-Lys-Leu-Gln-Glu-Gln-Gln-Ser-Asp

Glu-Gln-Glu-Arg-Leu-Ala-Lys-Glu-Lys-Leu-Gln-Glu-Gln-Gln-Ser-Asp-Leu

Gln-Glu-Arg-Leu-Ala-Lys-Glu-Lys-Leu-Gln-Glu-Gln-Gln-Ser-Asp-Leu-Glu

Glu-Arg-Leu-Ala-Lys-Glu-Lys-Leu-Gln-Glu-Gln-Gln-Ser-Asp-Leu-Glu-Gln

Arg-Leu-Ala-Lys-Glu-Lys-Leu-Gln-Glu-Gln-Gln-Ser-Asp-Leu-Glu-Gln-Leu

Leu-Ala-Lys-Glu-Lys-Leu-Gln-Gly-Gln-Gln-Ser-Asp-Leu-Glu-Gln-Glu-Arg

Ala-Lys-Glu-Lys-Leu-Gln-Gly-Gln-Gln-Ser-Asp-Leu-Glu-Gln-Glu-Arg-Leu

| (1)CTT | GCT | AAA | GAA | AAG | TTA | CAA | GAG | CAG | CAA | AGC | GAT | TTA | GAA | CAA | GAG | AGA |
|---|---|---|---|---|---|---|---|---|---|---|---|---|---|---|---|---|
| (2)... | ... | ... | ... | ... | ..G | ... | ..A | ..A | ... | ... | ... | C.. | ... | ... | ... | ... |
| (3)... | ... | ... | ... | ... | ..G | ... | ..A | ..A | ... | ... | ... | ... | ... | ... | ... | ... |
| (4)..A | ... | ... | ... | ... | ... | ..G | .G. | ..A | ... | ... | ... | C.. | ... | ... | ... | ... |

Bacteria acting as host to the above-mentioned clones DG 199 and DG 307 were deposited with the Collection Nationale des Cultures de Microorganismes de l'Institut Pasteur de Paris (CNCM), on the 22nd Jul. 1986 under the numbers I-580 and I-581, respectively. The DG 145 bacteria were deposited on the 15th Sep. 1986 under the number I-606.

What is claimed is:

1. An isolated or purified nucleotide sequence encoding a polypeptide produced in hepatocytes infected by *P. falciparum* comprising the sequence:

Leu-Ala-Lys-Glu-Lys-Leu-Gln-X-Gln-Gin-Ser-Asp-Leu-Glu-Gln-Glu-Arg in which:

X is "glu" (peptide sequence 1) or "gly" (peptide sequence II).

2. An isolated DNA molecule comprising a nucleotide sequence encoding a polypeptide comprising an amino acid sequence selected from the group consisting of:

Lys-Glu-Lys-Leu-Gln-Gly-Gln-Gln-Ser-Asp-Leu-Glu-Gln-Glu-Arg-Leu-Ala

Glu-Lys-Leu-Gln-Gly-Gln-Gln-Ser-Asp-Leu-Glu-Gln-Glu-Arg-Leu-Ala-Lys

Lys-Leu-Gln-Gly-Gln-Gln-Ser-Asp-Leu-Glu-Gln-Glu-Arg-Leu-Ala-Lys-Glu

Leu-Gln-Gly-Gln-Gln-Ser-Asp-Leu-Glu-Gln-Glu-Arg-Leu-Ala-Lys-Glu-Lys

Gln-Gly-Gln-Gln-Ser-Asp-Leu-Glu-Gln-Glu-Arg-Leu-Ala-Lys-Glu-Lys-Leu

Gly-Gln-Gln-Ser-Asp-Leu-Glu-Gln-Glu-Arg-Leu-Ala-Lys-Glu-Lys-Leu-Gln

Gln-Gln-Ser-Asp-Leu-Glu-Gln-Glu-Arg-Leu-Ala-Lys-Glu-Lys-Leu-Gln-Gly

Gln-Ser-Asp-Leu-Glu-Gln-Glu-Arg-Leu-Ala-Lys-Glu-Lys-Leu-Gln-Gly-Gln

Ser-Asp-Leu-Glu-Gln-Glu-Arg-Leu-Ala-Lys-Glu-Lys-Leu-Gln-Gly-Gln-Gln

Asp-Leu-Glu-Gln-Glu-Arg-Leu-Ala-Lys-Glu-Lys-Leu-Gln-Gly-Gln-Gln-Ser

Leu-Glu-Gln-Glu-Arg-Leu-Ala-Lys-Glu-Lys-Leu-Gln-Gly-Gln-Gln-Ser-Asp

Glu-Gln-Glu-Arg-Leu-Ala-Lys-Glu-Lys-Leu-Gln-Gly-Gln-Gln-Ser-Asp-Leu

Gln-Glu-Arg-Leu-Ala-Lys-Glu-Lys-Leu-Gln-Gly-Gln-Gln-Ser-Asp-Leu-Glu

Glu-Arg-Leu-Ala-Lys-Glu-Lys-Leu-Gln-Gly-Gln-Gln-Ser-Asp-Leu-Glu-Gln

Arg-Leu-Ala-Lys-Glu-Lys-Leu-Gln-Gly-Gln-Gln-Ser-Asp-Leu-Glu-Gln-Leu wherein said polypeptide induces antibodies that react with the schizont stage of *Plasmodium falciparum*, and wherein said polypeptide does not substantially react with antibodies to the blood or sporozoite stages of *Plasmodium falciparum*.

3. A DNA molecule of claim 1, wherein the polypeptide comprises at least two of said amino acid sequences.

4. A DNA molecule of claim 1, wherein the polypeptide comprises at least one multiple of said amino acid sequences.

5. A DNA molecule of claim 1, wherein the polypeptide comprises a chimeric polypeptide comprising at least one of said amino acid sequences.

6. A vector comprising a DNA molecule of any one of claims 1–5.

7. A host cell comprising the vector of claim 6.

* * * * *